(12) United States Patent
Ujifusa et al.

(10) Patent No.: US 10,512,483 B1
(45) Date of Patent: Dec. 24, 2019

(54) CERVICAL TENACULUM DEVICE

(71) Applicant: T & J Enterprises, LLC, Lake Stevens, WA (US)

(72) Inventors: Todd Michael Ujifusa, Lake Stevens, WA (US); Marek Andrzej Jaworski, University Place, WA (US)

(73) Assignee: T & J ENTERPRISES, LLC, Lake Stevens, WA (US)

( * ) Notice: Subject to any disclaimer, the term of this patent is extended or adjusted under 35 U.S.C. 154(b) by 0 days.

(21) Appl. No.: 16/291,797

(22) Filed: Mar. 4, 2019

Related U.S. Application Data

(60) Provisional application No. 62/760,647, filed on Nov. 13, 2018.

(51) Int. Cl.
*A61B 17/44* (2006.01)
*A61B 17/221* (2006.01)
*A61B 17/30* (2006.01)
*A61B 17/28* (2006.01)
*A61B 17/42* (2006.01)

(52) U.S. Cl.
CPC ............ *A61B 17/44* (2013.01); *A61B 17/221* (2013.01); *A61B 17/30* (2013.01); *A61B 17/282* (2013.01); *A61B 17/4241* (2013.01); *A61B 2017/4225* (2013.01)

(58) Field of Classification Search
CPC ....... A61B 17/44; A61B 17/08; A61B 17/083; A61B 17/086; A61B 17/42; A61B 2017/086
See application file for complete search history.

(56) References Cited

U.S. PATENT DOCUMENTS

| | | | | |
|---|---|---|---|---|
| 372,922 A * | 11/1887 | McCord | ............ | A61F 6/146 128/841 |
| 574,943 A * | 1/1897 | Ryman | ............ | A61F 6/146 128/841 |
| 2,041,424 A * | 5/1936 | McCormick | ............ | A61F 6/146 128/841 |
| 2,232,258 A * | 2/1941 | McCormick | ............ | A61F 6/146 128/841 |
| 2,844,144 A * | 7/1958 | Massey | ............ | A61B 17/42 600/221 |
| 4,000,743 A * | 1/1977 | Weaver | ............ | A61B 17/4241 606/119 |
| 4,274,415 A * | 6/1981 | Kanamoto | ............ | A61B 17/1227 606/142 |
| 4,444,187 A * | 4/1984 | Perlin | ............ | A61B 17/1227 606/158 |
| 5,026,379 A * | 6/1991 | Yoon | ............ | A61B 17/12013 606/141 |
| 5,382,257 A * | 1/1995 | Lewis | ............ | A61B 17/0401 606/148 |
| 5,683,405 A * | 11/1997 | Yacoubian | ............ | A61B 17/1227 24/545 |
| 5,730,747 A * | 3/1998 | Ek | ............ | A61B 17/0469 606/139 |
| 5,758,420 A * | 6/1998 | Schmidt | ............ | A61B 17/1227 29/896.9 |

(Continued)

*Primary Examiner* — Phong Son H Dang
(74) *Attorney, Agent, or Firm* — Kyle Straughan; Karr Tuttle Campbell

(57) ABSTRACT

A surgical device comprising: an applicator; a clamp comprising a clasp and a tether; and optionally an anchor.

11 Claims, 10 Drawing Sheets

(56) References Cited

U.S. PATENT DOCUMENTS

| | | | | |
|---|---|---|---|---|
| 5,947,982 A * | 9/1999 | Duran | A61B 17/0625 | 606/139 |
| 5,954,057 A * | 9/1999 | Li | A61B 17/062 | 128/898 |
| 6,391,035 B1 * | 5/2002 | Appleby | A61B 17/076 | 606/142 |
| 6,402,765 B1 * | 6/2002 | Monassevitch | A61B 17/064 | 606/151 |
| 6,984,237 B2 * | 1/2006 | Hatch | A61B 17/0469 | 606/144 |
| 7,354,444 B2 * | 4/2008 | Burbank | A61B 8/06 | 606/157 |
| 7,901,420 B2 * | 3/2011 | Dunn | A61B 17/1128 | 606/157 |
| 8,052,700 B2 * | 11/2011 | Dunn | A61B 17/1128 | 606/157 |
| 8,066,722 B2 * | 11/2011 | Miyagi | A61B 17/1285 | 606/142 |
| 8,636,754 B2 * | 1/2014 | Hughett, Sr. | A61B 17/1227 | 606/151 |
| 8,852,218 B2 * | 10/2014 | Hughett, Sr. | A61B 17/1227 | 606/157 |
| 8,864,776 B2 * | 10/2014 | Bogart | A61B 17/06004 | 606/144 |
| 8,968,340 B2 * | 3/2015 | Chowaniec | A61B 17/0469 | 606/144 |
| 9,289,216 B2 * | 3/2016 | Weisshaupt | A61B 17/1227 | |
| 9,393,023 B2 * | 7/2016 | Privitera | A61B 17/122 | |
| 9,402,757 B2 * | 8/2016 | Kassab | A61F 5/0086 | |
| 9,572,579 B2 * | 2/2017 | Weisshaupt | A61B 17/1227 | |
| 10,034,688 B2 | 7/2018 | O'Brien et al. | | |
| D835,270 S * | 12/2018 | Benson | D24/133 | |
| 10,166,024 B2 * | 1/2019 | Williamson, IV | A61B 17/083 | |
| 10,182,824 B2 * | 1/2019 | Monti | A61B 17/1227 | |
| 2002/0032454 A1 * | 3/2002 | Durgin | A61B 17/10 | 606/151 |
| 2002/0062130 A1 * | 5/2002 | Jugenheimer | A61B 17/122 | 606/142 |
| 2002/0177859 A1 * | 11/2002 | Monassevitch | A61B 17/064 | 606/139 |
| 2003/0120306 A1 * | 6/2003 | Burbank | A61B 5/489 | 606/205 |
| 2004/0092979 A1 * | 5/2004 | Burbank | A61B 8/06 | 606/158 |
| 2004/0097962 A1 * | 5/2004 | Burbank | A61B 17/1227 | 606/119 |
| 2004/0153105 A1 * | 8/2004 | Burbank | A61B 17/12 | 606/157 |
| 2004/0236349 A1 * | 11/2004 | Gellman | A61B 17/12013 | 606/119 |
| 2005/0251183 A1 * | 11/2005 | Buckman | A61B 17/08 | 606/157 |
| 2005/0277959 A1 * | 12/2005 | Cosgrove | A61B 17/12 | 606/151 |
| 2006/0259076 A1 * | 11/2006 | Burkhart | A61B 17/0401 | 606/228 |
| 2007/0106314 A1 * | 5/2007 | Dunn | A61B 17/1128 | 606/157 |
| 2007/0135843 A1 * | 6/2007 | Burkhart | A61B 17/0401 | 606/232 |
| 2007/0142844 A1 | 6/2007 | Kotmel et al. | | |
| 2007/0142860 A1 * | 6/2007 | Kotmel | A61B 17/42 | 606/205 |
| 2008/0004659 A1 * | 1/2008 | Burkhart | A61B 17/0401 | 606/232 |
| 2008/0132915 A1 * | 6/2008 | Buckman | A61B 17/08 | 606/138 |
| 2009/0012545 A1 * | 1/2009 | Williamson, IV | A61B 17/083 | 606/157 |
| 2009/0105720 A1 * | 4/2009 | Boone | A61B 17/42 | 606/119 |
| 2009/0318914 A1 * | 12/2009 | Utley | A61B 18/1206 | 606/33 |
| 2009/0318965 A1 * | 12/2009 | Burkhart | A61B 17/0483 | 606/232 |
| 2010/0010511 A1 * | 1/2010 | Harris | A61B 17/083 | 606/143 |
| 2010/0076344 A1 * | 3/2010 | Kecman | A61B 1/32 | 600/569 |
| 2011/0046437 A1 * | 2/2011 | Kassab | A61F 5/0086 | 600/37 |
| 2011/0079226 A1 * | 4/2011 | Sakhel | A61B 1/303 | 128/830 |
| 2012/0035631 A1 * | 2/2012 | Hughett, Sr. | A61B 17/1227 | 606/157 |
| 2012/0109147 A1 * | 5/2012 | Auerbach | A61B 17/4241 | 606/119 |
| 2012/0123445 A1 * | 5/2012 | Hughett, Sr. | A61B 17/1227 | 606/142 |
| 2012/0165868 A1 * | 6/2012 | Burkhart | A61B 17/0401 | 606/232 |
| 2013/0172682 A1 * | 7/2013 | Ransden | A61B 17/0218 | 600/204 |
| 2013/0172683 A1 * | 7/2013 | Gresham | A61B 17/3498 | 600/204 |
| 2013/0345747 A1 * | 12/2013 | Dreyfuss | A61B 17/0401 | 606/232 |
| 2016/0220347 A1 * | 8/2016 | Hoover | A61F 2/0811 | |
| 2016/0331408 A1 * | 11/2016 | Benson | A61B 17/4241 | |
| 2017/0189007 A1 * | 7/2017 | Burkhart | A61B 17/0401 | |
| 2019/0105046 A1 * | 4/2019 | Jagelski | A61B 17/083 | |

* cited by examiner

CERVICAL TENACULUM DEVICE

PRIORITY CLAIM

This application claims priority to and/or the benefit of U.S. Provisional Patent Application Ser. No. 62/760,647 filed Nov. 13, 2018. The foregoing application is incorporated by reference in its entirety as if fully set forth herein.

BACKGROUND OF THE INVENTION

This invention relates generally to a medical device, and more specifically, to a surgical tenaculum.

BRIEF SUMMARY

This invention relates generally to a medical device, and more specifically, to a surgical tenaculum. Specific details of certain embodiments of the invention are set forth in the following description and in the figures to provide a thorough understanding of such embodiments. The present invention may have additional embodiments, may be practiced without one or more of the details described for any particular described embodiment, or may have any detail described for one particular embodiment practiced with any other detail described for another embodiment.

The surgical tenaculum is a medical instrument used for a variety of purposes, but among its most common is the manipulation of a patient's cervix and uterus during medical procedures, including, but not limited to Dilation & Curettage, Endometrial Biopsy, Abortion, Hysteroscopy, Operative Hysteroscopy, Endometrial Ablation, LEEP/LLETZ Procedure, Colposcopy, Intrauterine Insemination Procedure, Intrauterine Device Insertion, Saline Infusion Sonography, Hysterosalpingogram, and Hysterectomy. During many of the above procedures manipulation of the cervix is key because they typically involve pushing an object through the cervix and into the uterus, and thus require counter-traction be applied to the cervix. Alternatively, in some procedures the tenaculum is used to straighten the patient's uterus to allow the physician access. In simplest terms, the cervix must be grasped, held in place, and pulled towards the practitioner to allow the procedure to move forward.

Typically, during a surgical procedure or when the practitioner requires access to the cervix or uterus, the instruments, including the tenaculum, are inserted into the vagina or other body cavity through a speculum. During the procedure other tools are often inserted into the speculum including, but not limited to, a clamp, catheters, cannula, biopsy devices, diagnostic camera and imaging tools, light sources, and/or irrigation tubes which can further obstruct the practitioners view of the cervix. In addition, the number of tools that require they be actively held can result in the practitioner, any aides, or even the patient being required to hold a large number of items at once, which can limit the effectiveness of the practitioner. Among many benefits, the present invention allows the necessary, adjustable counter-traction to be placed on the cervix by allowing the tenaculum to attach to a speculum or other stationary component, including possibly the patient's skin, or a strap or harness, thereby potentially freeing a hand of practitioner.

In some embodiments, the surgical device comprises an applicator; a clamp comprising a clasp and a tether; and an anchor.

BRIEF DESCRIPTION OF THE DRAWINGS

Embodiments of the present invention are described in detail below with reference to the following drawings.

DETAILED DESCRIPTION

Figure 1:
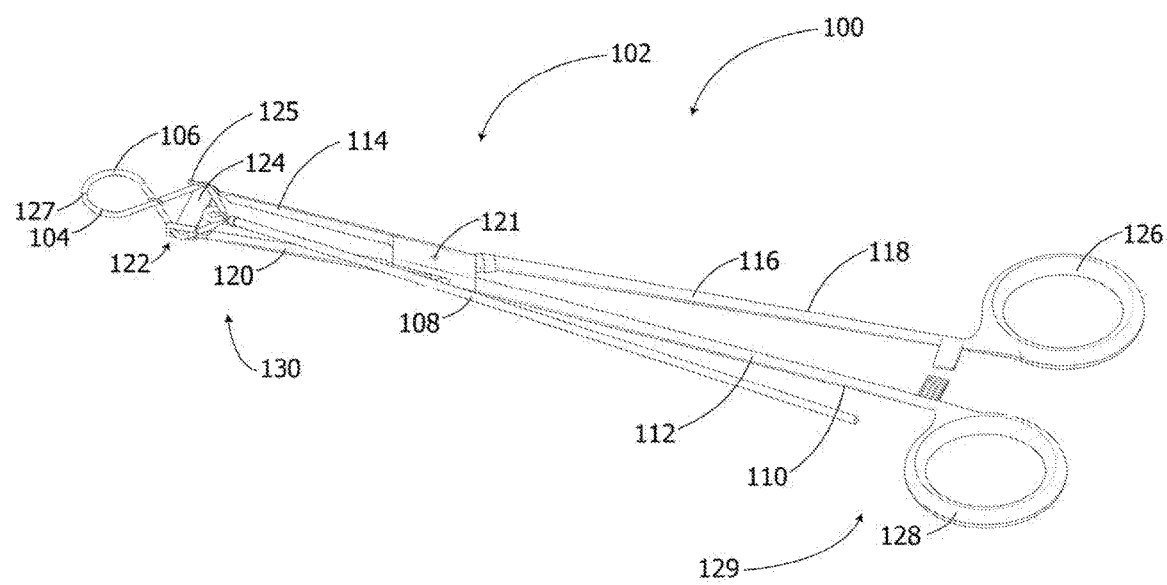
FIG. 1 is a perspective view of a cervical tenaculum device, in accordance with an embodiment of the invention.

This invention relates generally to a medical device, and more specifically, to a surgical tenaculum. Specific details of certain embodiments of the invention are set forth in the following description and in FIGS. 1-8 to provide a thorough understanding of such embodiments. The present invention may have additional embodiments, may be practiced without one or more of the details described for any particular described embodiment, or may have any detail described for one particular embodiment practiced with any other detail described for another embodiment.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

In some embodiments, the invention comprises an applicator comprising a forceps or modified forceps with an application device at a proximal end opposite a handle mechanism at a distal end; a clamp comprised of a clasp that is configured to be at least one of engaged or disengaged through the use of the applicator, and a tether capable of holding or applying tension. In some embodiments the invention may further comprise an anchor or other means to secure the tether.

In some embodiments the handle mechanism is comprised of a scissors-style forceps handle, while in other embodiments it may be a based on a twisting movement, push-pull movement, plunger, quick-release screw, or other means of engaging the distal end and in turn the application device. In some embodiments the handle mechanism may have multiple components allowing it to be held in various configurations such as being configured to remove the handle once the applicator is in place, remove the applicator entirely once the clamp is in place, or leave the entire device in the patient. For example, the handle mechanism may be a screw attached to or embedded in another body such as, but not limited to, a spring, and said screw may have a grip such as, but not limited to, a bow-handle grip or nut grip, wherein twisting the grip is used to engage or disengage the application device or the clamp itself.

In some embodiments the application device, or applicator, is integrated into the forceps while in others the application device is a separate component that may be attached and detached from the handle. In some embodiments the application device is a flange or pylon that extends between the distal ends of the forceps grip and functions as a guide for the clamp. In some embodiments, the applicator is configured to engage the clamp to the object to be grabbed, such as in the case of gynecology, the cervix, by performing the means used to engage the clamp such as, but not limited to, placing pressure on the distal end of a clamp, pressing the distal levers of a scissor hinge or placing closing tension thereon, or automatically engaging a ratchet or screw for other variants. In some embodiments the application device is divided into a separate applicator and the handle, the former of which may engage the clamp, or in some embodiments the clamp and applicator are a singular device.

In some embodiments, a practitioner or user engages the device by pressing the first shank and second shank towards each other, which in turn causes the first tip and second tip to press together which exerts pressure on the clamp which opens the clasp component. The tips of the clasp can then be applied to a cervix or other article to be held, and once it is in a location the practitioner deems appropriate the first shank and second shank can be released, which relieves the pressure keeping the clamp open and closes the clasp, thereby taking hold of the article. The first shank and second shank can then be pulled away from each other which allows the clamp to slip from the first aperture and second aperture, leaving the clamp, clasp, and/or tether still inside the patient, and attached to the article. The practitioner can then remove the applicator and attach the distal end of the tether to an anchor or other tension-holding means to maintain tension on the article being grasped by the clamp.

In some embodiments the clamp is a clamp or other configuration wherein the clamp may automatically favor a closed position over an open one and exerts tension on the points or pressure exerting areas of the clasp's tip. In some embodiments, the clamp has a mechanism such as a screw, ratchet, or other variable tension means to place tension on the grasping means. In some embodiments the mechanism is in the form of pointed tips such as found in a common surgical tenaculum, while in other embodiments it may involve a shaped pad or rod allowing it to displace the force over the surface it is grasping and diminish any trauma to the area or article being grasped. In some embodiments the clasp may be a tether that encircles the area to be held like a noose or similar means. In some embodiments the clasp is a pinch-based grasping means with two prongs, while in others it may have additional prongs as needed to sufficiently grasp and hold the article in question. In some embodiments, the clamp is comprised of one or more hinges pivoted together such that when tension is placed on corresponding ends of the hinges the opposite ends are closed. In some embodiments, the clamp is comprised of one or more hinges, such as scissor-hinges, that are connected with each other and operable against each other such that operating one hinge will operate another.

In some embodiments, the clamp does not automatically favor a closed position. In some embodiments, the clamp is also a scissors-style hinge mechanism wherein a distal end is designed to be a grasping end while a proximal end is the end engaged by the applicator. In such embodiments the tension placed on the proximal end by the tether keeps the jaws of the distal end closed. In some embodiments, the scissors-style hinge clamp may have a quick-release mechanism, retrieval cord, or other means of disengaging tension. In some embodiments, the scissors-style hinge clamp may have a means of disengaging tension including a latch, catch, screw, and/or may be pushed on by the tether in order to release the tension.

In some embodiments the clasp is attached to a tether to form the clamp. In some embodiments this tether is comprised of silicone or another substance from the list including, but not limited to, silicone, rubber or plastic. In some embodiments, the tether is a chain made of one or more substances from the list including, but not limited to, metal or plastic. The tether can be pulled to place tension on the clasp and allow a user to in turn place tension on the article which the clasp is grasping, such as, but not limited to, in the case of gynecological procedures, a cervix. In some embodiments the clasp is attached to the tether by a variable tension means such as, but not limited to, a spring. In some embodiments, the tether is comprised of a chain from the list including, but not limited to, a box chain or a ball chain.

In some embodiments the clamp is configured with a release mechanism such as, but not limited to, a secondary tether, a screw, a catch, a latch or other means that allows the clamp to release or otherwise cease placing any pressure on the clasp or article, in some cases to facilitate removal of the clamp or to allow readjustment of the placement of the clasp. In some embodiments, the tether is configured so that it can be pushed towards the clasp, releasing pressure on the clasp and/or causing the clasp to release the article being held.

In some embodiments the entire device is disposable, while in others it is designed to be reused. In some embodiments certain components are disposable while other components in the same embodiment may be reusable. In some embodiments, the components of the device may be comprised of one or more substances from the list including, but not limited to, silicone, plastic, metal, composites, or combinations thereof.

In some embodiments, the device is further comprised of an anchor that is comprised of a securing mechanism configured to be attached to a speculum or other surgical instrument or may be configured to adhere to skin or other surfaces. The securing mechanism may be, but is not limited to, a mechanical clip, an adhesive patch, a pin, a needle to thread through a medium, a screw, and/or a clasp. The securing mechanism may alternatively be a combination of the aforementioned components configured in a complementary way. In some embodiments the anchor includes a thread, hole, notch, clasp, or other means to secure the tether to the anchor, allowing the anchor to hold tension on the tether and by extension the article that the clasp is holding. In some embodiments, the anchor is configured to attach to a range of other surgical stabilizers or instruments including, but not limited to, a speculum. In some embodiments the handle section and/or applicator may function as the anchor.

In some embodiments the device may be configured to integrate with other tools for a variety of purposes, such as integrating with a gynecological speculum to reduce the tenaculum's profile and further improve the visibility through the speculum.

FIG. 1 is a perspective view of a cervical tenaculum device applicator, in accordance with an embodiment of the invention.

In some embodiments, a surgical device 100 is comprised of an applicator 102; a clamp 104 comprising a clasp 106 and a tether 108; and an anchor.

In some embodiments, the surgical device 100 applicator 102 further comprises a first lever 110 comprised of a first shank 112 connected to a first tip 114 and a second lever 116 comprised of a second shank 118 connected to a second tip 120, wherein the first lever 110 and second lever 116 are pivoted to each other in a central position 121 and, wherein the second tip 120 is further comprised of a second aperture 122 and the first tip 114 has a pylon 124 extending outward towards the second tip 120 and in some embodiments at least partly through the second aperture 122 when the device 100 is closed, and a first aperture 125.

In some embodiments, the first lever 110 is further comprised of a first bow-handle grip 126 connected to the first shank 112 and the second lever 116 is further comprised of a second bow-handle grip 128 connected to the second shank 118.

In some embodiments, the invention comprises an applicator 102 comprised of forceps or modified forceps with an application device 130 (the combination may comprise, but is not limited to, the second tip 120, second aperture 122, first tip 114, pylon 124 and first aperture 125) added to a proximal end opposite a handle mechanism 129 on a distal end (the combination may comprise, but is not limited to, of the first shank 112, second shank 118, first bow-handle grip 126 and the second bow handle grip 128); a clamp 104 comprised of a clasp 106 that is configured to be at least one of engaged or disengaged through the use of the applicator 102, and a tether 108 capable of holding or applying tension.

In some embodiments, a practitioner or user engages the device 100 by pressing the first shank 112 and second shank 118 towards each other, which in turn causes the first tip 114 and second tip 120 to press together which exerts pressure on the clamp 104 which opens the clasp 106 component. The tips 127 of the clasp 106 can then be applied to a cervix or other article to be held, and once it is in a location the practitioner deems appropriate the first shank 112 and second shank 118 can be released, which relieves the pressure keeping the clamp 104 open and closes the clasp 106, thereby taking hold of the article. The first shank 112 and second shank 118 can then be pulled away from each other which allows the clamp 104 to slip from the first aperture 125 and second aperture 122, leaving the clamp 104, clasp 106, and tether 108 still inside the patient. The practitioner can then remove the applicator 102 and attach the distal end of the tether to an anchor or other tension-holding means to maintain tension on the article being grabbed by the clamp 104.

In some embodiments the handle mechanism 129 is comprised of a scissors-style forceps handle, while in other embodiments it may be a based on a twisting movement, push-pull movement, plunger, quick-release screw, or other means of engaging the distal end and in turn the application device 130. In some embodiments the handle mechanism 129 may have multiple components allowing it to be held in various configurations such as being configured to remove the handle mechanism 129 once the application device 130 is in place, remove the applicator 102 entirely once the clamp 104 is in place, or leave the entire device 100 in the patient. For example, the handle mechanism 129 may be a screw attached to or embedded in another body such as, but not limited to, a spring, and said screw may have a grip (e.g. references 126 and 128) such as, but not limited to, a bow-handle grip or nut grip, wherein twisting the grip is used to engage or disengage the application device 130 or the clamp 104 itself.

In some embodiments the application device 130, is integrated into the forceps while in others the application device 130 is a separate component that may be attached and detached from the handle mechanism 129. In some embodiments the application device 130 is a flange or pylon 124 that extends between the distal ends of the forceps grip and functions as a guide for the clamp 104. In some embodiments, the application device 130 is configured to engage the clamp 104 to the object to be grabbed, such as in the case of gynecology, the cervix, by performing the means used to engage the clamp 104 such as, but not limited to, placing pressure on the distal end of a cross-locking clasp 106, or automatically engaging a ratchet or screw for other variants. In some embodiments the applicator 102 is divided into a separate application device 130 and the handle 129, the former of which may engage the clamp 104, or in some embodiments the clamp 104 and application device 130 are a singular device.

In some embodiments the clamp 104 is a cross-locking clasp 106 or other configuration wherein the clasp 106 may automatically favor a closed position over an open one and exerts tension on the points or pressure exerting areas of the clamp's 104 tips 127. In some embodiments, the clamp 104 has a mechanism such as a screw, ratchet, or other variable tension means to place tension on the clasp 106. In some embodiments the clasp's 106 grasping mechanism is in the form of pointed tips 127 such as found in a common surgical tenaculum, while in other embodiments it may involve a shaped pad or rod allowing it to displace the force over the surface it is grasping and diminish any trauma to the area. In some embodiments the clasp 106 may be a tether that encircles the area to be held like a noose or similar means. In some embodiments the clasp 106 is a pinch-based grasping means with two prongs, while in others it may have additional prongs as needed to sufficiently grasp and hold the article in question. In some embodiments, the clamp 104 is comprised of one or more hinges pivoted together such that when tension is placed on corresponding ends of the hinges the opposite ends are closed.

In some embodiments the clasp 106 is attached to a tether 108. In some embodiments this tether 108 is a cord comprised a substance from a list including, but not limited to, silicone, rubber or plastic. In some embodiments, the tether 108 is a chain made of one or more substances from the list including, but not limited to, metal or plastic. The tether 108 can be held to place tension on the clasp and allow a user to in turn place tension on the article which the clasp 106 is grasping, such as, but not limited to, in the case of gynecological procedures, a cervix. In some embodiments the clasp is attached to the tether by a variable tension means such as, but not limited to, a spring.

In some embodiments the clamp 104 is configured with a release mechanism such as, but not limited to, a secondary tether 108, a screw, a catch, a latch or other means that allows the clamp 104 to release or otherwise cease placing any pressure on the clasp 106, in some cases to facilitate removal of the clamp 104 or to allow readjustment of the placement of the clasp 106.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

Figure 2:
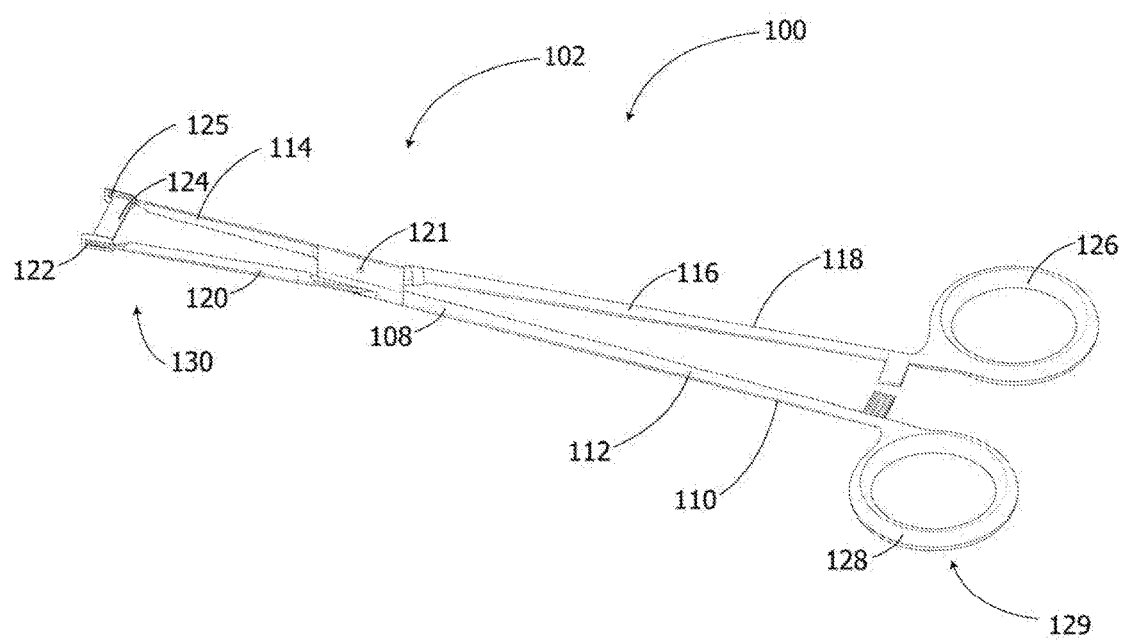
FIG. 2 is a perspective view of a cervical tenaculum device applicator, in accordance with an embodiment of the invention.

FIG. 2 is a perspective view of a cervical tenaculum device applicator, in accordance with an embodiment of the invention.

In some embodiments, a surgical device 100 is comprised of an applicator 102; a clamp comprising a clasp and a tether, and optionally an anchor.

In some embodiments, the surgical device 100 applicator 102 further comprises a first lever 110 comprised of a first shank 112 connected to a first tip 114 and a second lever 116 comprised of a second shank 118 connected to a second tip 120, wherein the first lever 110 and second lever 116 are pivoted to each other in a central position 121 and, wherein the second tip 120 is further comprised of a second aperture 122 and the first tip 114 has a pylon 124 extending outward towards the second tip 120 and at least partly through the second aperture 122 when the device 100 is closed and a first aperture 125.

In some embodiments, the first lever 110 is further comprised of a first bow-handle grip 126 connected to the first shank 112 and the second lever 116 is further comprised of a second bow-handle grip 128 connected to the second shank 118.

In some embodiments, the invention comprises an applicator 102 comprised of forceps or modified forceps with an application device 130 (the combination may comprise, but is not limited to, the second tip 120, second aperture 122, first tip 114, pylon 124 and first aperture 125) added to a proximal end opposite a handle mechanism 129 on a distal end (the combination may comprise, but is not limited to, of the first shank 112, second shank 118, first bow-handle grip 126 and the second bow handle grip 128); a clamp comprised of a clasp that is configured to be at least one of engaged or disengaged through the use of the applicator 102, and a tether capable of holding or applying tension.

In some embodiments, a practitioner or user engages the device 100 by pressing the first shank 112 and second shank 118 towards each other, which in turn causes the first tip 114 and second tip 120 to press together which exerts pressure on the clamp 104 which opens the clasp 106 component. The tips 127 of the clasp 106 can then be applied to a cervix or other article to be held and once it is in a location the practitioner deems appropriate the first shank 112 and second shank 118 can be released, which relieves the pressure keeping the clamp 104 open and closes the clasp 106, thereby taking hold of the article. The first shank 112 and second shank 118 can then be pulled away from each other which allows the clamp 104 to slip from the first aperture 125 and second aperture 122, leaving the clamp 104, clasp 106, and tether 108 still inside the patient. The practitioner can then remove the applicator 102 and attach the distal end of the tether to an anchor or other tension-holding means to maintain tension on the article being grabbed by the clamp 104.

In some embodiments the handle mechanism 129 is comprised of a scissors-style forceps handle, while in other embodiments it may be a based on a twisting movement, push-pull movement, plunger, quick-release screw, or other means of engaging the distal end and in turn the application device 130. In some embodiments the handle mechanism 129 may have multiple components allowing it to be held in various configurations such as being configured to remove the handle mechanism 129 once the application device 130 is in place, remove the applicator 102 entirely once the clamp 104 is in place, or leave the entire device 100 in the patient. For example, the handle mechanism 129 may be a screw attached to or embedded in another body such as, but not limited to, a spring, and said screw may have a grip (e.g. references 126 and 128) such as, but not limited to, a bow-handle grip or nut grip, wherein twisting the grip is used to engage or disengage the application device 130 or the clamp 104 itself.

In some embodiments the application device 130, is integrated into the forceps while in others the application device 130 is a separate component that may be attached and detached from the handle mechanism 129. In some embodiments the application device 130 is a flange or pylon 124 that extends between the distal ends of the forceps grip and functions as a guide for the clamp.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

Figure 3:
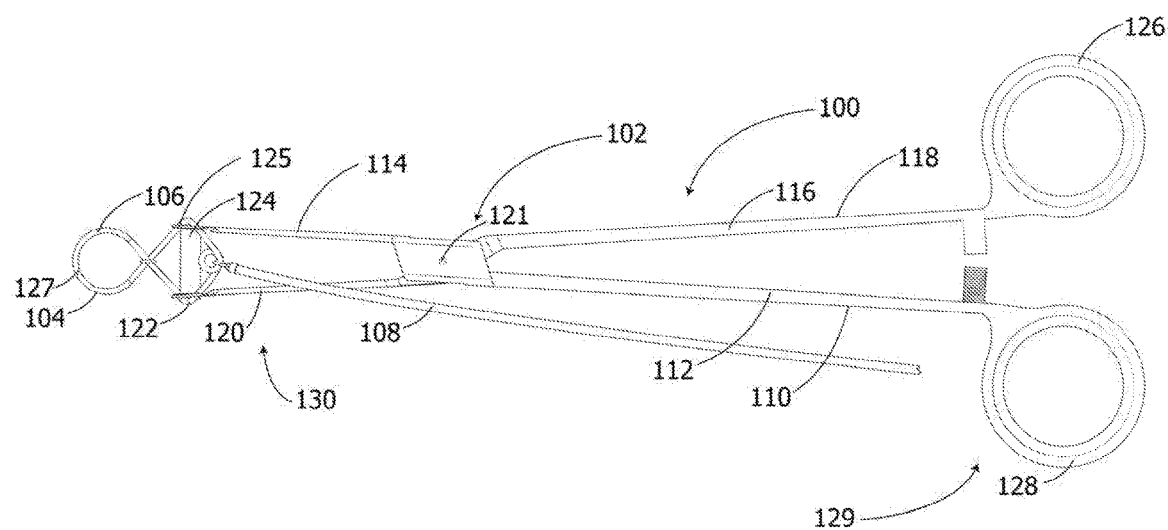
FIG. 3 is a top view of a cervical tenaculum device, in accordance with an embodiment of the invention.

FIG. 3 is a top view of a cervical tenaculum device, in accordance with an embodiment of the invention.

In some embodiments, a surgical device 100 is comprised of an applicator 102; a clamp 104 comprising a clasp 106 and a tether 108; and an anchor.

In some embodiments, the surgical device 100 applicator 102 further comprises a first lever 110 comprised of a first shank 112 connected to a first tip 114 and a second lever 116 comprised of a second shank 118 connected to a second tip 120, wherein the first lever 110 and second lever 116 are pivoted to each other in a central position 121 and, wherein the second tip 120 is further comprised of a second aperture and the first tip 114 has a pylon 124 extending outward towards the second tip 120 and at least partly through the second aperture when the device 100 is closed and a first aperture.

In some embodiments, the first lever 110 is further comprised of a first bow-handle grip 126 connected to the first shank 112 and the second lever 116 is further comprised of a second bow-handle grip 128 connected to the second shank 118.

In some embodiments, the invention comprises an applicator 102 comprised of forceps or modified forceps with an application device 130 (the combination may comprise, but is not limited to, the second tip 120, second aperture, first tip 114, pylon 124 and first aperture) added to a proximal end opposite a handle mechanism 129 on a distal end (the combination may comprise, but is not limited to, of the first shank 112, second shank 118, first bow-handle grip 126 and the second bow handle grip 128); a clamp 104 comprised of a clasp 106 that is configured to be at least one of engaged or disengaged through the use of the applicator 102, and a tether 108 capable of holding or applying tension.

In some embodiments the handle mechanism 129 is comprised of a scissors-style forceps handle, while in other embodiments it may be a based on a twisting movement, push-pull movement, plunger, quick-release screw, or other means of engaging the distal end and in turn the application device 130. In some embodiments the handle mechanism 129 may have multiple components allowing it to be held in various configurations such as being configured to remove the handle mechanism 129 once the application device 130 is in place, remove the applicator 102 entirely once the clamp 104 is in place, or leave the entire device 100 in the patient. For example, the handle mechanism 129 may be a screw attached to or embedded in another body such as, but not limited to, a spring, and said screw may have a grip (e.g. references 126 and 128) such as, but not limited to, a bow-handle grip or nut grip, wherein twisting the grip is used to engage or disengage the application device 130 or the clamp 104 itself.

In some embodiments the application device 130, is integrated into the forceps while in others the application device 130 is a separate component that may be attached and detached from the handle mechanism 129. In some embodiments the application device 130 is a flange or pylon 124 that extends between the distal ends of the forceps grip and functions as a guide for the clamp 104. In some embodiments, the application device 130 is configured to engage the clamp 104 to the object to be grabbed, such as in the case of gynecology, the cervix, by performing the means used to engage the clamp 104 such as, but not limited to, placing pressure on the distal end of a cross-locking clasp 106, or automatically engaging a ratchet or screw for other variants. In some embodiments the applicator 102 is divided into a separate application device 130 and the handle 129, the former of which may engage the clamp 104, or in some embodiments the clamp 104 and application device 130 are a singular device.

In some embodiments the clamp 104 is a cross-locking clasp 106 or other configuration wherein the clasp 106 may automatically favor a closed position over an open one and exerts tension on the points or pressure exerting areas of the clamp's 104 tips 127. In some embodiments, the clamp 104 has a mechanism such as a screw, ratchet, or other variable tension means to place tension on the clasp 106. In some embodiments the clasp's 106 mechanism is in the form of pointed tips 127 such as found in a common surgical tenaculum, while in other embodiments it may involve a shaped pad or rod allowing it to displace the force over the surface it is grasping and diminish any trauma to the area. In some embodiments the clasp 106 may be a tether that encircles the area to be held like a noose or similar means. In some embodiments the clasp 106 is a pinch-based grasping means with two prongs, while in others it may have additional prongs as needed to sufficiently grasp and hold the article in question. In some embodiments, the clamp 104 is comprised of one or more hinges pivoted together such that when tension is placed on corresponding ends of the hinges the opposite ends are closed.

In some embodiments the clasp 106 is attached to a tether 108. In some embodiments this tether 108 is a cord comprised a substance from a list including, but not limited to, silicone, rubber or plastic. In some embodiments, the tether 108 is a chain made of one or more substances from the list including, but not limited to, metal or plastic. The tether 108 can be held to place tension on the clasp and allow a user to in turn place tension on the article which the clasp is grasping, such as, but not limited to, in the case of gynecological procedures, a cervix. In some embodiments the clasp is attached to the tether 108 by a variable tension means such as, but not limited to, a spring.

In some embodiments the clamp 104 is configured with a release mechanism such as, but not limited to, a secondary tether 108, a screw, a catch, a latch or other means that allows the clamp 104 to release or otherwise cease placing any pressure on the clasp 106, in some cases to facilitate removal of the clamp 104 or to allow readjustment of the placement of the clasp 106.

In some embodiments the entire device 100 is disposable, while in others it is designed to be reused. In some embodiments certain components are disposable while other components in the same embodiment may be reusable. In some embodiments, the components of the device 100 may be comprised of one or more substances from the list including, but not limited to, silicone, plastic, metal, composites, or combinations thereof.

Figure 4:
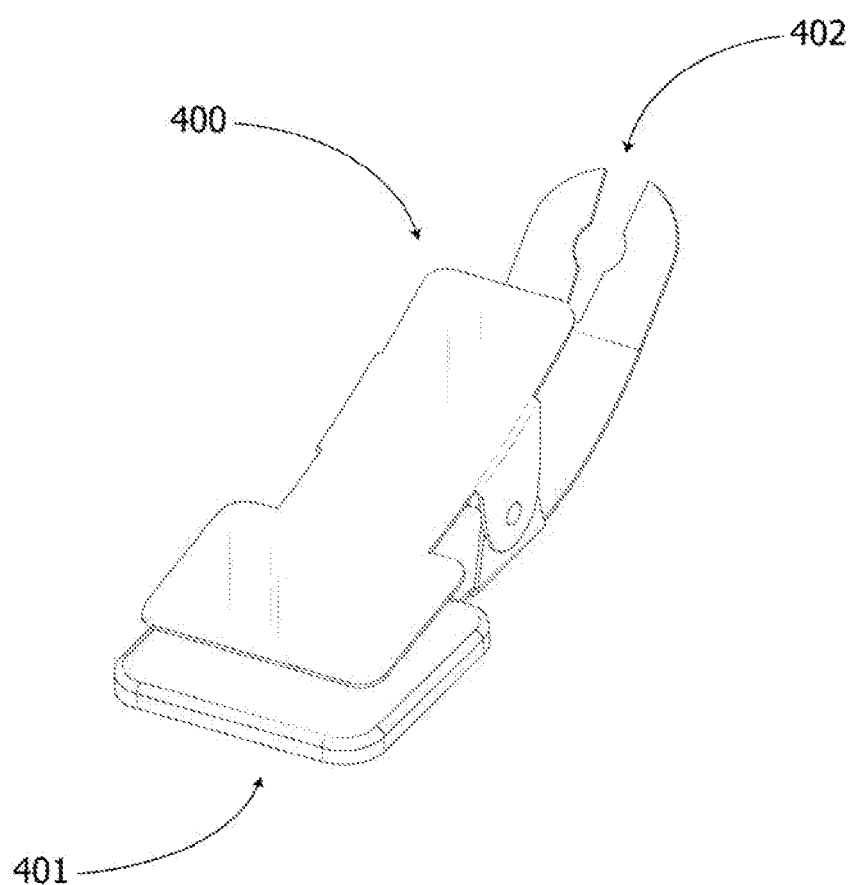
FIG. 4 is a perspective view of a cervical tenaculum device anchor, in accordance with an embodiment of the invention.
Figure 9:
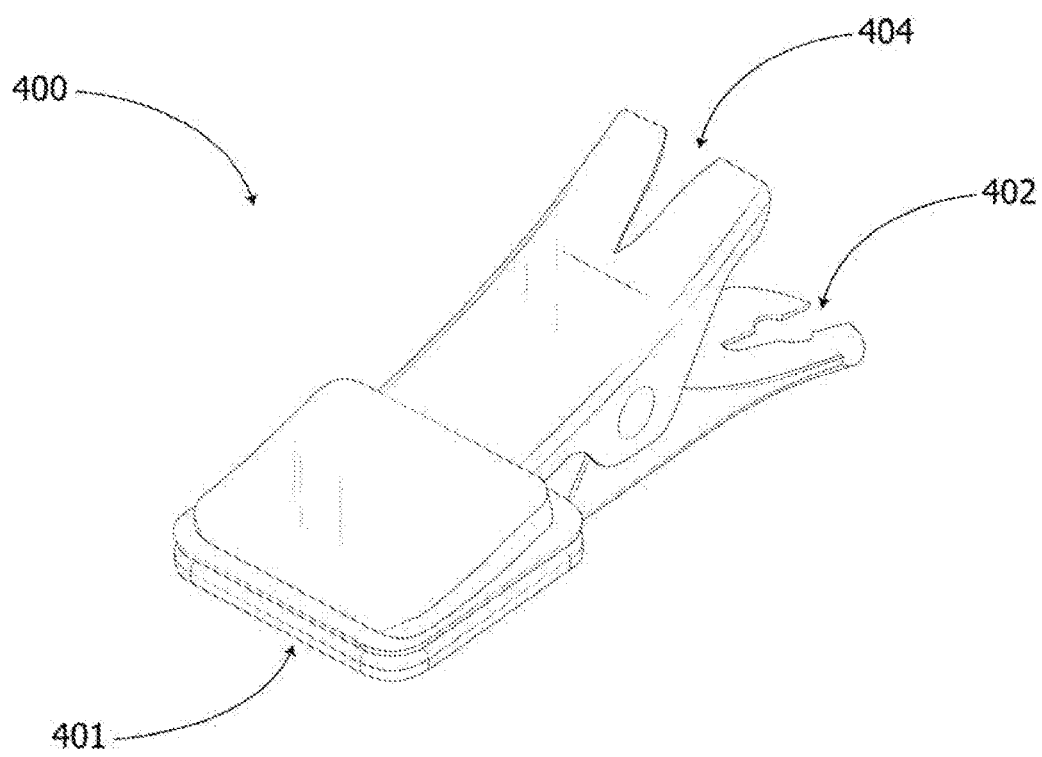
FIG. 9 is a perspective view of a cervical tenaculum device anchor, in accordance with an embodiment of the invention.

FIGS. 4 and 9 are perspective views of variants of a cervical tenaculum device anchor, in accordance with an embodiment of the invention.

In some embodiments, a surgical device is comprised of an applicator 102; a clamp comprising a clasp and a tether; and an anchor 400 (with variants shown in FIGS. 4 and 9.)

In some embodiments, the device is further comprised of an anchor 400 that is comprised of a securing mechanism 401 allowing it to be attached to a speculum or other surgical instrument or may be configured to adhere to skin or other surfaces. The securing mechanism 401 may be, but is not limited to, a mechanical clip, an adhesive patch, pin, a needle to thread through a medium, a screw, and/or a clasp. The securing mechanism 401 may alternatively be a combination of the aforementioned components configured in a complementary way. In some embodiments the anchor 400 is further comprised of an attachment point 402. In some embodiments the attachment point 402 is configured as a thread, hole, notch, clasp, or other means to secure the tether to the anchor 400, allowing the anchor 400 to hold tension on the tether and by extension the article that the clasp is holding. In some embodiments, the anchor 400 is configured to attach to a range of other surgical stabilizers or instruments including, but not limited to, a speculum. In some embodiments the handle section and/or applicator may function as the anchor 400.

In some embodiments, the anchor 400 is further comprised of one or more attachment points 402 that allows the tether to be threaded through it in order to maintain the pressure. In some embodiments the anchor 400 is further comprised of a second attachment point 404 that allows the slack of the tether to be angled away from a practitioner. The attachment points 402 and 404 may be a groove, flange, hook, notch, or other holding means that the tether can be inserted into.

Figure 5:
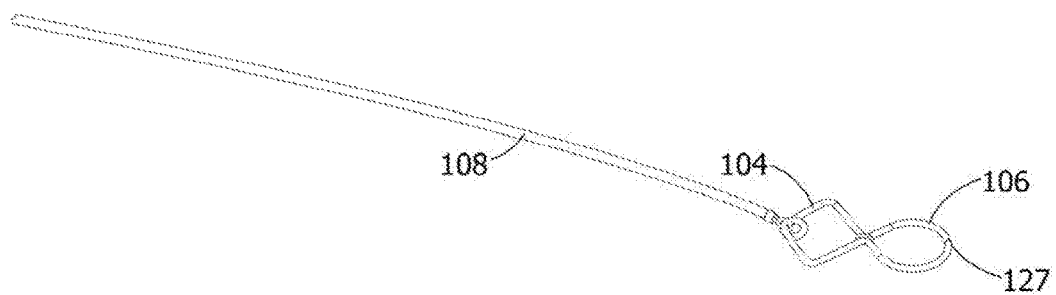
FIG. 5 is a perspective view of a cervical tenaculum device clamp, in accordance with an embodiment of the invention.
Figure 10:
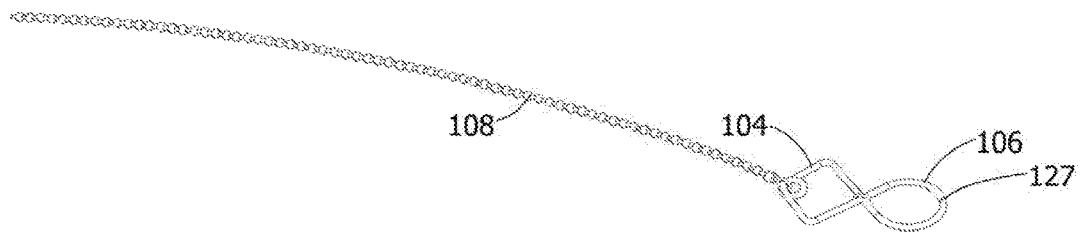
FIG. 10 is a perspective view of a cervical tenaculum device clamp, in accordance with an embodiment of the invention.

FIGS. 5 and 10 are perspective views of two variants of a cervical tenaculum device tether, in accordance with an embodiment of the invention.

In some embodiments, the application device is configured to engage the clamp 104 to the object to be grabbed, such as in the case of gynecology, the cervix, by performing the means used to engage the clamp 104 such as, but not limited to, placing pressure on the distal end of a cross-locking clasp 106, or automatically engaging a ratchet or screw for other variants. In some embodiments the applicator 102 is divided into a separate application device and the handle, the former of which may engage the clamp 104, or in some embodiments the clamp 104 and application device are a singular device.

In some embodiments the clamp 104 is a cross-locking clasp 106 or other configuration wherein the clasp 106 may automatically favor a closed position over an open one and exerts tension on the points or pressure exerting areas of the clamp's 104 tips 127. In some embodiments, the clamp 104 has a mechanism such as a screw, ratchet, or other variable tension means to place tension on the clasp 106. In some embodiments the clasp's 106 mechanism is in the form of pointed tips 127 such as found in a common surgical tenaculum, while in other embodiments it may involve a shaped pad or rod allowing it to displace the force over the surface it is grasping and diminish any trauma to the area. In some embodiments the clasp 106 may be a tether that encircles the area to be held like a noose or similar means. In some embodiments the clasp 106 is a pinch-based grasping means with two prongs, while in others it may have additional prongs as needed to sufficiently grasp and hold the article in question. In some embodiments, the clamp 104 is comprised of one or more hinges pivoted together such that when tension is placed on corresponding ends of the hinges the opposite ends are closed.

In some embodiments the clasp 106 is attached to a tether 108. In some embodiments this tether 108 is a cord comprised a substance from a list including, but not limited to, silicone, rubber or plastic. In some embodiments, the tether 108 is a chain made of one or more substances from the list including, but not limited to, metal or plastic. The tether 108 can be held to place tension on the clasp and allow a user to in turn place tension on the article which the clasp 106 is grasping, such as, but not limited to, in the case of gynecological procedures, a cervix. In some embodiments the clasp is attached to the tether 108 by a variable tension means such as, but not limited to, a spring.

In some embodiments the clamp 104 is configured with a release mechanism such as, but not limited to, a secondary tether 108, a screw, a catch, a latch or other means that allows the clamp 104 to release or otherwise cease placing any pressure on the clasp 106, in some cases to facilitate removal of the clamp 104 or to allow readjustment of the placement of the clasp 106.

Figure 6:
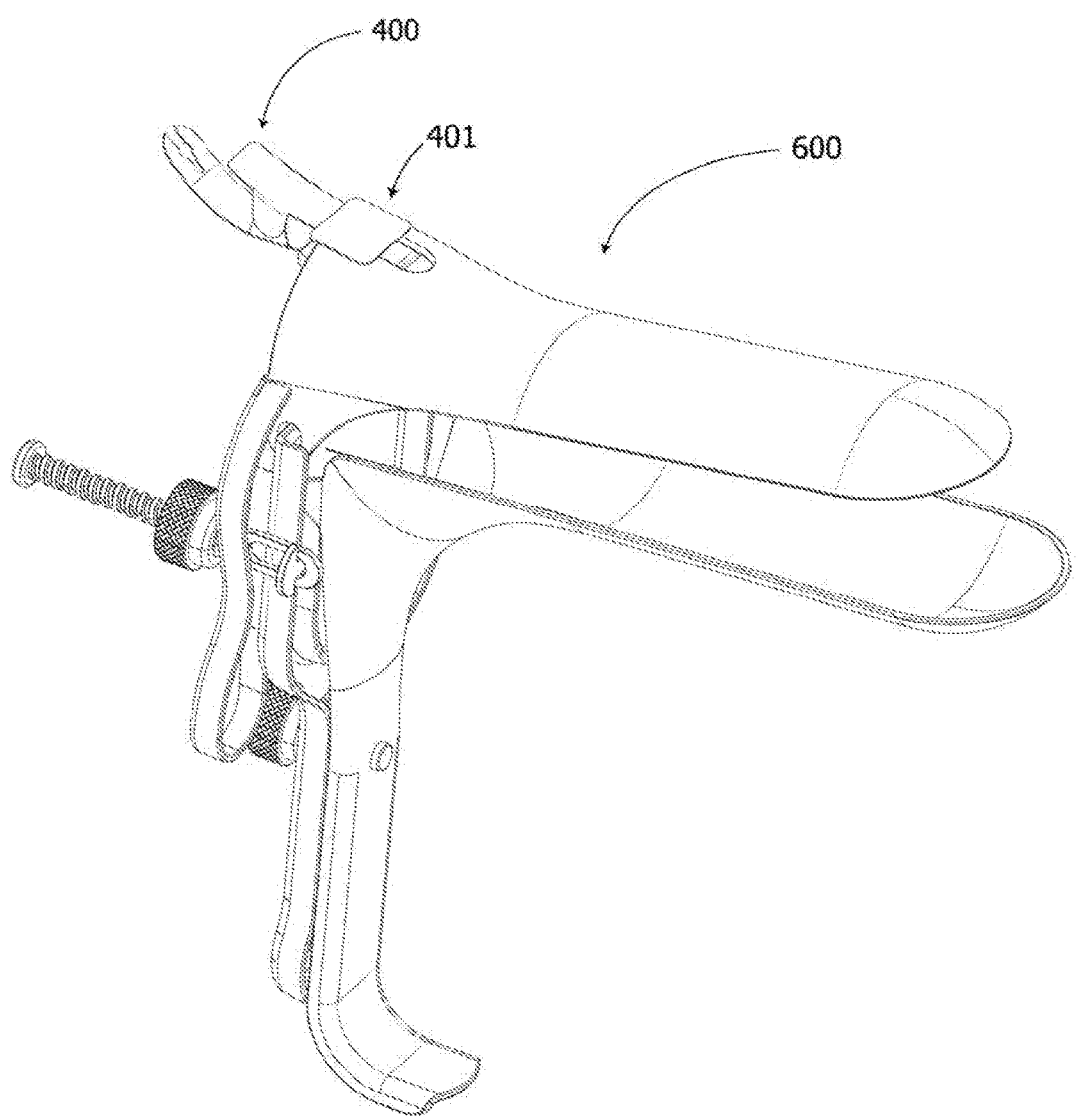
FIG. 6 is a perspective view of a speculum, in accordance with an embodiment of the invention.

FIG. 6 is a perspective view of a speculum, in accordance with an embodiment of the invention.

In some embodiments, the device is configured to integrate with a surgical speculum 600 wherein the anchor 400 is able to clasp to the opening aperture at the distal end of the speculum 600.

In some embodiments, the device is further comprised of an anchor 400 that is comprised of a securing mechanism 401 allowing it to be attached to a speculum or other surgical instrument or may be configured to adhere to skin or other surfaces. The securing mechanism 401 may be, but is not limited to, a mechanical clip, an adhesive patch, pin, a needle to thread through a medium, a screw, and/or a clasp. The securing mechanism 401 may alternatively be a combination of the aforementioned components configured in a complementary way. In some embodiments the anchor 400 includes a thread, hole, notch, clasp, or other means to secure the tether to the anchor 400, allowing the anchor 400 to hold tension on the tether and by extension the article that the clasp is holding. In some embodiments, the anchor 400 is configured to attach to a range of other surgical stabilizers or instruments including, but not limited to, a speculum. In some embodiments the handle section and/or applicator may function as the anchor 400.

In some embodiments, the anchor 400 is further comprised of one or more attachment points 402 that allows the tether to be threaded through it in order to maintain the pressure. In some embodiments the anchor 400 is further comprised of a second attachment point 404 that allows the slack of the tether to be angled away from a practitioner. The attachment points 402 and 404 may be a groove, flange, hook, notch, or other holding means that the tether can be inserted into.

Figure 7:
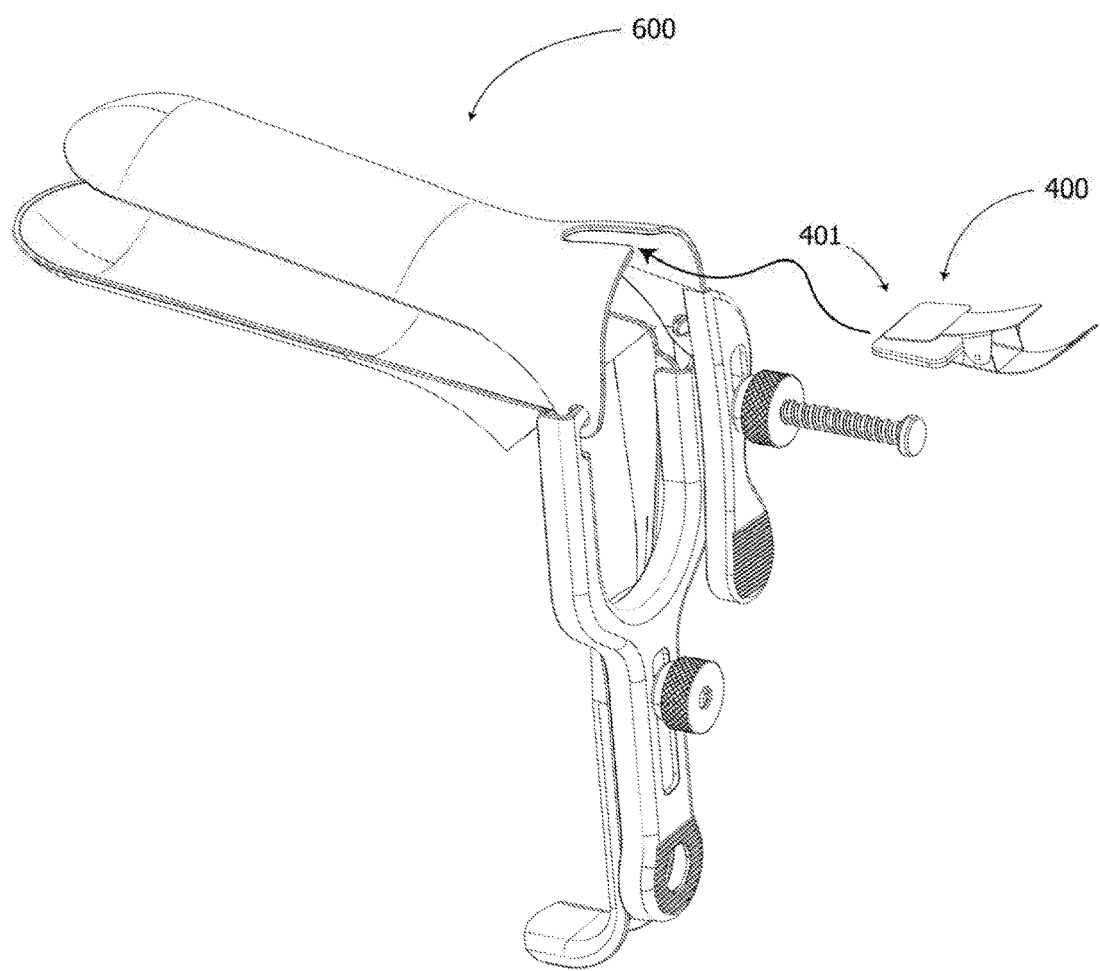
FIG. 7 is a perspective view of a speculum with a cervical tenaculum device clamp, in accordance with an embodiment of the invention.

FIG. 7 is a perspective view of a speculum with a cervical tenaculum device clamp, in accordance with an embodiment of the invention.

In some embodiments, the device is configured to integrate with a surgical speculum 600 wherein the anchor 400 is able to clasp to the opening aperture at the distal end of the speculum 600.

In some embodiments, the device is further comprised of an anchor 400 that is comprised of a securing mechanism 401 allowing it to be attached to a speculum or other surgical instrument or may be configured to adhere to skin or other surfaces. The securing mechanism 401 may be, but is not limited to, a mechanical clip, an adhesive patch, pin, a needle to thread through a medium, a screw, and/or a clasp. The securing mechanism 401 may alternatively be a combination of the aforementioned components configured in a complementary way. In some embodiments the anchor 400 includes a thread, hole, notch, clasp, or other means to secure the tether to the anchor 400, allowing the anchor 400 to hold tension on the tether and by extension the article that the clasp is holding. In some embodiments, the anchor 400 is configured to attach to a range of other surgical stabilizers or instruments including, but not limited to, a speculum. In some embodiments the handle section and/or applicator may function as the anchor 400.

In some embodiments, the anchor 400 is further comprised of one or more attachment points 402 that allows the tether to be threaded through it in order to maintain the pressure. In some embodiments the anchor 400 is further comprised of a second attachment point 404 that allows the slack of the tether to be angled away from a practitioner. The attachment points 402 and 404 may be a groove, flange, hook, notch, or other holding means that the tether can be inserted into.

Figure 8:
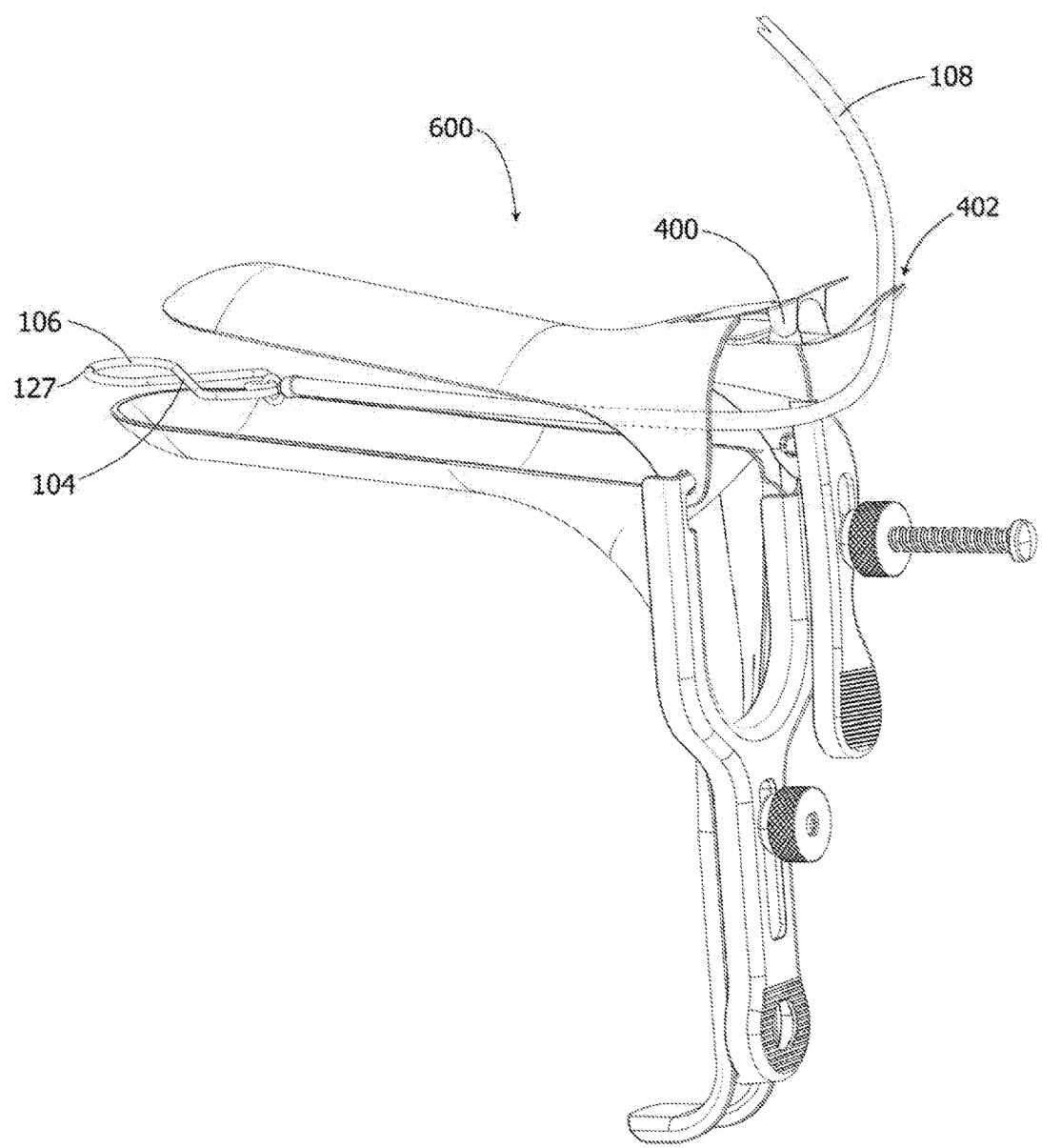
FIG. 8 is a perspective view of a cervical tenaculum device through a speculum, in accordance with an embodiment of the invention.

FIG. 8 is a perspective view of a cervical tenaculum device through a speculum, in accordance with an embodiment of the invention.

In some embodiments, the application device is configured to engage the clamp 104 to the object to be grabbed, such as in the case of gynecology, the cervix, by performing the means used to engage the clamp 104 such as, but not limited to, placing pressure on the distal end of a cross-locking clasp 106, or automatically engaging a ratchet or screw for other variants. In some embodiments the applicator 102 is divided into a separate application device and the handle, the former of which may engage the clamp 104, or in some embodiments the clamp 104 and application device are a singular device.

In some embodiments the clamp 104 is a cross-locking clasp 106 or other configuration wherein the clasp 106 may automatically favor a closed position over an open one and exerts tension on the points or pressure exerting areas of the clamp's 104 tips 127. In some embodiments, the clamp 104 has a mechanism such as a screw, ratchet, or other variable tension means to place tension on the clasp 106. In some embodiments the clasp's 106 mechanism is in the form of pointed tips 127 such as found in a common surgical tenaculum, while in other embodiments it may involve a shaped pad or rod allowing it to displace the force over the surface it is grasping and diminish any trauma to the area. In some embodiments the clasp 106 may be a tether that encircles the area to be held like a noose or similar means. In some embodiments the clasp 106 is a pinch-based grasping means with two prongs, while in others it may have additional prongs as needed to sufficiently grasp and hold the article in question. In some embodiments, the clamp 104 is comprised of one or more hinges pivoted together such that when tension is placed on corresponding ends of the hinges the opposite ends are closed.

In some embodiments the clasp 106 is attached to a tether 108. In some embodiments this tether 108 is a cord comprised a substance from a list including, but not limited to, silicone, rubber or plastic. In some embodiments, the tether 108 is a chain made of one or more substances from the list including, but not limited to, metal or plastic. The tether 108 can be held to place tension on the clasp and allow a user to in turn place tension on the article which the clasp 106 is grasping, such as, but not limited to, in the case of gynecological procedures, a cervix. In some embodiments the clasp is attached to the tether 108 by a variable tension means such as, but not limited to, a spring.

In some embodiments the clamp 104 is configured with a release mechanism such as, but not limited to, a secondary tether 108, a screw, a catch, a latch or other means that allows the clamp 104 to release or otherwise cease placing any pressure on the clasp 106, in some cases to facilitate removal of the clamp 104 or to allow readjustment of the placement of the clasp 106.

In some embodiments, the device is configured to integrate with a surgical speculum 600 wherein the anchor 400 is able to clasp to the opening aperture at the distal end of the speculum 600.

In some embodiments, the device is further comprised of an anchor 400 that is comprised of a securing mechanism allowing it to be attached to a speculum or other surgical instrument or may be configured to adhere to skin or other surfaces. The securing mechanism may be, but is not limited to, a mechanical clip, an adhesive patch, pin, a needle to thread through a medium, a screw, and/or a clasp. The securing mechanism may alternatively be a combination of the aforementioned components configured in a complementary way. In some embodiments the anchor 400 includes a thread, hole, notch, clasp, or other means to secure the tether to the anchor 400, allowing the anchor 400 to hold tension on the tether and by extension the article that the clasp is holding. In some embodiments, the anchor 400 is configured to attach to a range of other surgical stabilizers or instruments including, but not limited to, a speculum. In some embodiments the handle section and/or applicator may function as the anchor 400.

In some embodiments, the anchor 400 is further comprised of one or more attachment points 402 that allows the tether to be threaded through it in order to maintain the pressure. In some embodiments the anchor 400 is further comprised of a second attachment point that allows the slack of the tether to be angled away from a practitioner. The attachment point 402 may be a groove, flange, hook, notch, or other holding means that the tether can be inserted into.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects. It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

Accordingly, the scope of the invention is not limited by the disclosure of these preferred and alternate embodiments. Instead, the invention should be determined by reference to the claims that follow.

What is claimed is:

1. A surgical device comprising:
an applicator comprised of a first tip and a second tip wherein the second tip is further comprised of a second aperture and the first tip is further comprised of a first pylon extending outward towards the second tip and at least partly through the second aperture when the device is closed, and a first aperture; and
a clamp removably coupled to the first tip and second tip of the applicator, the clamp comprising a clasp and a tether, wherein the clasp of the clamp is cross-locking.

2. The device of claim 1, wherein the applicator is further comprised of:
a first lever comprised of a first shank connected to a first tip and a second lever comprised of a second shank connected to a second tip.

3. The device of claim 2, wherein the first lever and second lever are pivoted to each other in a central position.

4. The device of claim 3, wherein the first lever is further comprised of a first bow-handle grip connected to the first shank and the second lever is further comprised of a second bow-handle grip connected to the second shank.

5. The device of claim 2, wherein the first lever and the second lever are substantially straight.

6. The device of claim 2, wherein the clamp is further comprised of one or more engagement points comprised of one or more pointed tips.

7. The device of claim 1, wherein the tether is a chain.

8. The device of claim 1, wherein the tether is at least partially elastic.

9. The device of claim 1, wherein the device is further comprised of: an anchor.

10. The device of claim 9, wherein the anchor has a connection point configured to hold the tether of the clamp.

11. The device of claim 9, wherein the anchor is an alligator-style clip.

* * * * *